(12) United States Patent
Otsubo (10) Patent No.: US 7,758,558 B2
(45) Date of Patent: Jul. 20, 2010

(54) PANTS-TYPE DISPOSABLE WEARING ARTICLE

(75) Inventor: Toshifumi Otsubo, Kagawa (JP)

(73) Assignee: Uni-Charm Co., Ltd. (JP)

( * ) Notice: Subject to any disclaimer, the term of this patent is extended or adjusted under 35 U.S.C. 154(b) by 1022 days.

(21) Appl. No.: 10/730,260

(22) Filed: Dec. 9, 2003

(65) Prior Publication Data

US 2004/0167494 A1 Aug. 26, 2004

Related U.S. Application Data

(63) Continuation of application No. PCT/JP02/07733, filed on Jul. 30, 2002.

(30) Foreign Application Priority Data

Jul. 31, 2001 (JP) .............................. 2001-231078

(51) Int. Cl.
*A61F 13/15* (2006.01)
*A61F 13/20* (2006.01)
(52) U.S. Cl. .............................. 604/385.27; 604/385.24
(58) Field of Classification Search ................................ 604/385.24–385.27
See application file for complete search history.

(56) References Cited

U.S. PATENT DOCUMENTS

| | | | |
|---|---|---|---|
| 4,762,581 A * | 8/1988 | Stancliffe et al. .............. | 156/84 |
| 5,171,239 A | 12/1992 | Igaue et al. | |
| 5,415,649 A | 5/1995 | Watanabe et al. | |
| 5,437,910 A * | 8/1995 | Raabe et al. ................. | 428/194 |
| 5,575,783 A | 11/1996 | Clear et al. | |
| 5,745,922 A | 5/1998 | Rajala et al. | |
| 5,846,232 A | 12/1998 | Serbiak et al. | |
| 5,910,224 A * | 6/1999 | Morman ..................... | 156/178 |
| 6,049,916 A | 4/2000 | Rajala et al. | |
| 6,297,424 B1 * | 10/2001 | Olson et al. .................. | 604/361 |
| 6,595,976 B2 | 7/2003 | Jitoe et al. | |
| 6,923,797 B2 | 8/2005 | Shinohara et al. | |
| 2002/0049421 A1 | 4/2002 | Hayase et al. | |

FOREIGN PATENT DOCUMENTS

| | | |
|---|---|---|
| EP | 0761194 | 8/1996 |
| EP | 0762293 | 8/1996 |
| EP | 0 990 434 | 4/2000 |
| EP | 0990434 | 4/2000 |

(Continued)

OTHER PUBLICATIONS

English translation of JP 2000-107225 (Jitoue et al).*

(Continued)

*Primary Examiner*—Melanie J Hand
(74) *Attorney, Agent, or Firm*—Lowe Hauptman Ham & Berner, LLP (57) ABSTRACT

A pants-type disposable wearing article includes a chassis forming a body of the article, an absorbent structure disposed on an inner surface of the chassis, and a plurality of elastic members arranged in waist-surrounding regions. Opposite end portions of the elastic members in a waist surrounding direction are secured in the vicinities of transversely opposite side edges of the waist regions to the chassis while middle portions of the elastic members in the waist surrounding direction are not secured to the corresponding portions of the chassis.

24 Claims, 8 Drawing Sheets

FOREIGN PATENT DOCUMENTS

| | | |
|---|---|---|
| EP | 1 157 681 | 11/2001 |
| EP | 1157681 | 11/2001 |
| EP | 1184012 | 3/2002 |
| EP | 1 197 195 | 4/2002 |
| EP | 1197195 | 4/2002 |
| JP | 07236650 A * | 9/1995 |
| JP | 08-084747 | 4/1996 |
| JP | 1997-38134 | 2/1997 |
| JP | 09-056747 | 3/1997 |
| JP | 09-099006 | 4/1997 |
| JP | 11-299829 | 11/1999 |
| JP | 2000-107225 | 4/2000 |
| JP | 2000107225 A * | 4/2000 |
| JP | 2001-145666 | 5/2001 |
| JP | 2001145666 A * | 5/2001 |
| JP | 2001-157690 | 6/2001 |
| JP | 2002-095692 | 4/2002 |
| JP | 2003-038556 | 2/2003 |

OTHER PUBLICATIONS

English translation of JP 2001-145666 (Ando et al).*
Patent Abstract of Japan; Publication No. 09-056747 published Mar. 4, 1997 withJapanese Application No. 07-221976 filed Aug. 30, 1995.
Patent Abstract of Japan; Publication No. 2002-095692 published Apr. 2, 2002 with Japanese Application No. 2000-290745 filed Sep. 25, 2000.
Patent Abstract of Japan; Publication No. 2001-145666 published May 29, 2001 with Japanese Application No. 11-329189 filed Nov. 19, 1999.
Patent Abstract of Japan; Publication No. 2001-157690 published Jun. 12, 2001 with Japanese Application No. 11-343511 filed Dec. 2, 1999.
Patent Abstract of Japan; Publication No. 08-084747 published Apr. 2, 1996 with Japanese Application No. 06-246732 filed Sep. 16, 1994.

* cited by examiner

PANTS-TYPE DISPOSABLE WEARING ARTICLE

This application is a continuation of International Application No. PCT/JP02/07733 filed Jul. 30, 2002, which claims priority to Japanese Application No. 2001-231078 filed Jul. 31, 2001.

TECHNICAL FIELD OF THE INVENTION

This invention relates to a pants-type disposable wearing article for absorption and containment of bodily discharges.

BACKGROUND ART OF THE INVENTION

Japanese Patent Publication No. 1997-56747A discloses a pants-type disposable wearing article comprising a liquid-pervious inner sheet facing a wearer's body, a liquid-impervious outer sheet facing away from the wearer's body and a liquid-absorbent core interposed between these inner and outer sheets. These inner and outer sheets are joined together in the vicinity of transversely opposite side edge portions of front and rear waist regions at a plurality of heat-sealing sites arranged intermittently in the longitudinal direction so as to form a waist-hole and a pair of leg-holes lying below the waist-hole.

In this wearing article, a plurality of elastic members are attached in a stretched state to a waist-hole's peripheral edge portion in a waist-surrounding direction and to leg-hole's peripheral edge portions in a thigh-surrounding direction, respectively. The thigh-surrounding elastic members are secured to respective inner surfaces of the inner and outer sheets by means of a hot melt adhesive. The waist-surrounding elastic members are sideways arranged between the waist-hole and the leg-holes, being spaced one from another by a dimension given in the longitudinal direction. In a core-free area of the front waist region, the waist-surrounding elastic members are secured to the respective inner surfaces of the inner and outer sheets by means of a hot melt adhesive. In the core-occupied area of the front waist region, the waist-surrounding elastic members are secured to the inner surface of the outer sheet by means of a hot melt adhesive.

In this wearing article, a spacing at which the waist-surrounding elastic members are arranged in the vicinity of the core's longitudinally opposite ends is smaller than the corresponding spacing in the other area of the core so that the wearing article can be reliably put in close contact with the wearer's body in the vicinity of the longitudinally opposite ends of the core and a leakage of bodily discharges possibly occurring in the vicinity of the core's ends can be reliably prevented.

In the wearing article disclosed in the above-cited Publication, a plurality of fine gathers are formed on the inner and outer sheets in the core-free area as well as the outer sheet in the core-occupied area when the waist-surrounding elastic members contract in the waist-surrounding direction. In this wearing article, these fine gathers may not only deteriorate touch as well as appearance of the inner and outer sheets but also distort a picture or a geometric pattern depicted as a fancy element on the outer surface of the outer sheet as much as the fancy element can not be distinctly recognized.

It is an object of this invention to provide a pants-type disposable wearing article improved so that a plurality of fine gathers may not be formed in a generally middle zone of a front waist region at least and an fancy element depicted in the front waist region may be distinctly recognized.

DISCLOSURE OF THE INVENTION

According to this invention, there is provided a pants-type disposable wearing article having a longitudinal direction, a waist-surrounding direction orthogonal to the longitudinal direction, a front waist region, a rear waist region, a crotch region, an elasticized waist-hole and a pair of elasticized leg-holes, the article comprising a chassis and an absorbent structure extending on an inner surface of the chassis between the front and rear waist regions, and a plurality of auxiliary elastic members secured to the chassis in a stretched state in the waist surrounding direction so as to cross the absorbent structure in at least one of the front and rear waist regions, the article further comprising:

the plurality of auxiliary elastic members having opposite end portions and a middle portions in the waist-surrounding direction, the opposite end portions being secured to the chassis in vicinities of opposite side edges of the one of the front and rear waist regions while the middle portion being free to the chassis in the one of the front and rear waist regions.

This invention includes the following embodiments:

The chassis comprises an outer sheet and an inner sheet joined at a plurality of joining sites.

The plurality of joining sites are distributed at least an area of the absorbent structure in the one of the front and rear waist regions so as to be spaced one from another by a given space in the longitudinal direction between the auxiliary elastic members.

The plurality of joining sites are distributed in the vicinity of transversely opposite side edges of the absorbent structure.

A length of the auxiliary elastic members in the waist-surrounding direction as measured in a contracted state thereof is generally equal to a corresponding length of the absorbent structure in the one of the front and rear waist regions.

In the one of the front and rear waist regions, a fancy element is depicted on the chassis in the area of the absorbent structure.

The absorbent structure comprises a liquid-pervious inner sheet facing a wearer's body, a substantially liquid-impervious outer sheet opposed to the inner sheet and a liquid-absorbent core.

The absorbent structure comprises a liquid-pervious inner sheet and a liquid-absorbent core having a top surface thereof covered with the inner sheet.

The front and rear waist regions of the chassis are joined at the transversely opposite side edges to each other.

A pair of leakage-barrier flaps extend along the transversely opposite side edges of the absorbent structure.

DESCRIPTION OF THE BEST MODE FOR WORKING OF THE INVENTION

Details of a pants-type disposable article will be more fully understood from the description given hereunder in reference to the accompanying drawings.

The first embodiment according to this invention is illustrated in FIGS. 1-4.

Figure 1:
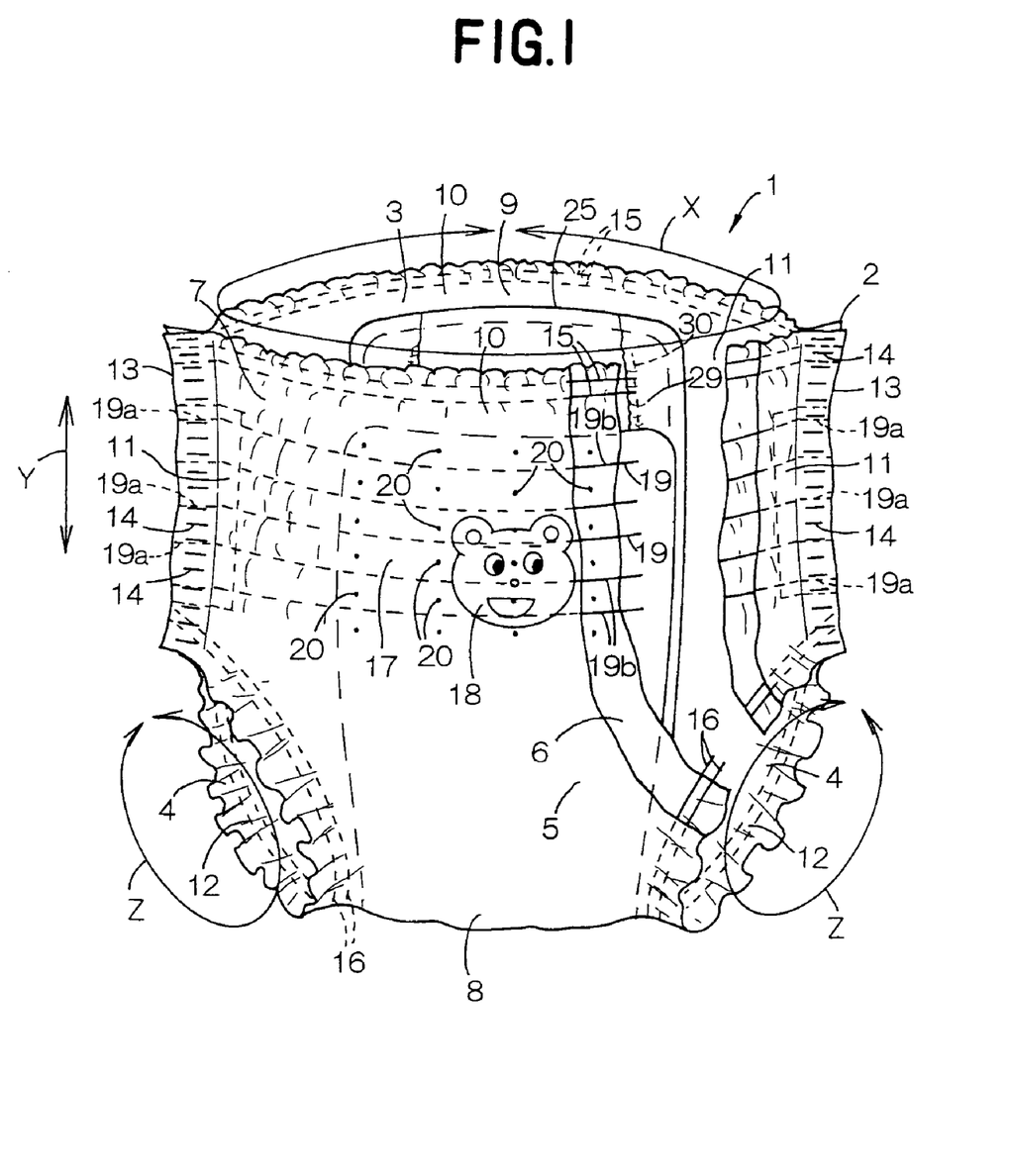
FIG. 1 is a partially cutaway perspective view showing a disposable wearing article.
Figure 2:
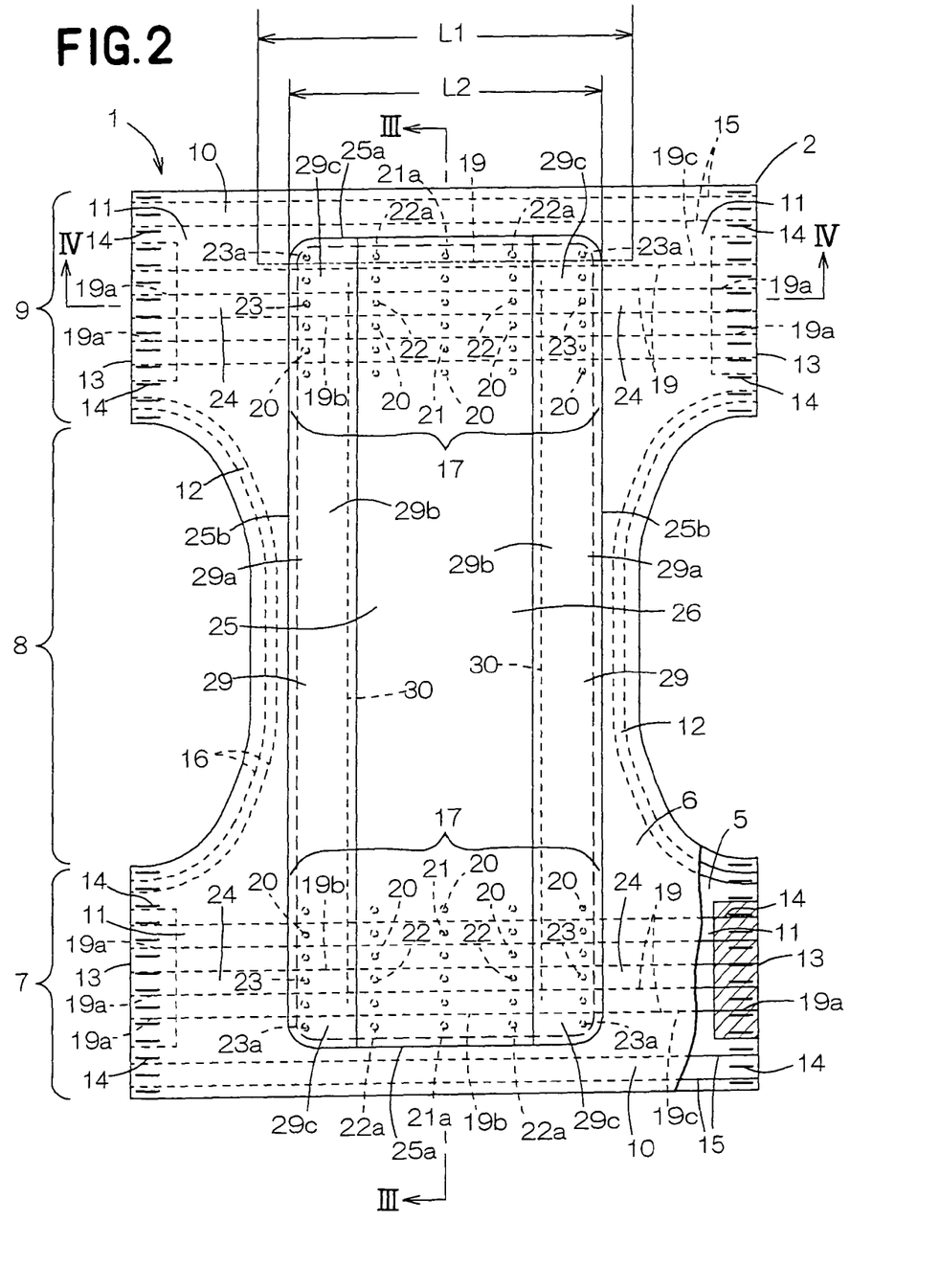
FIG. 2 is a plan view showing the article of FIG. 1 as developed in a longitudinal direction.
Figure 3:
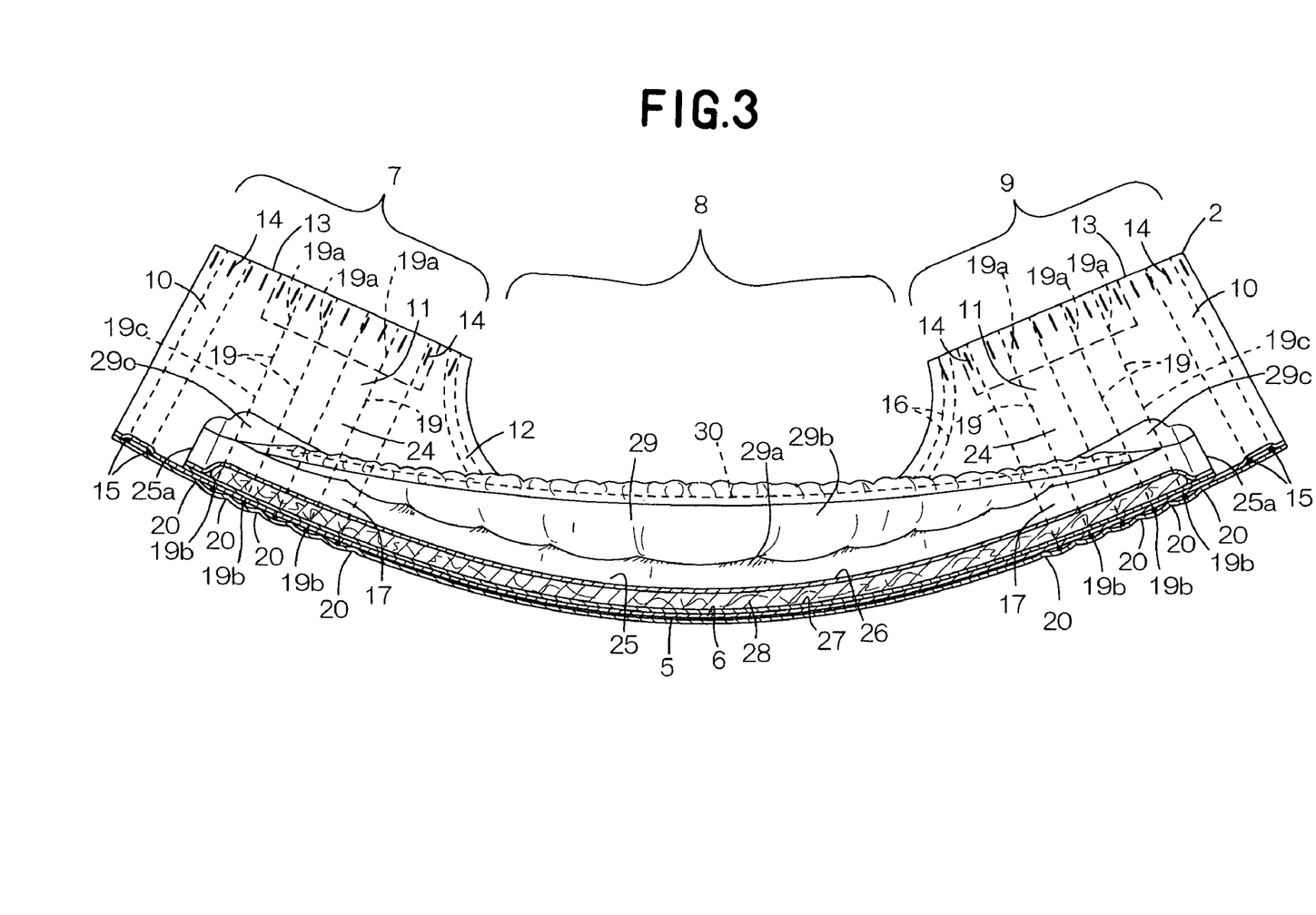
FIG. 3 is a cross-sectional view taken along a line III-III in FIG. 2.
Figure 4:
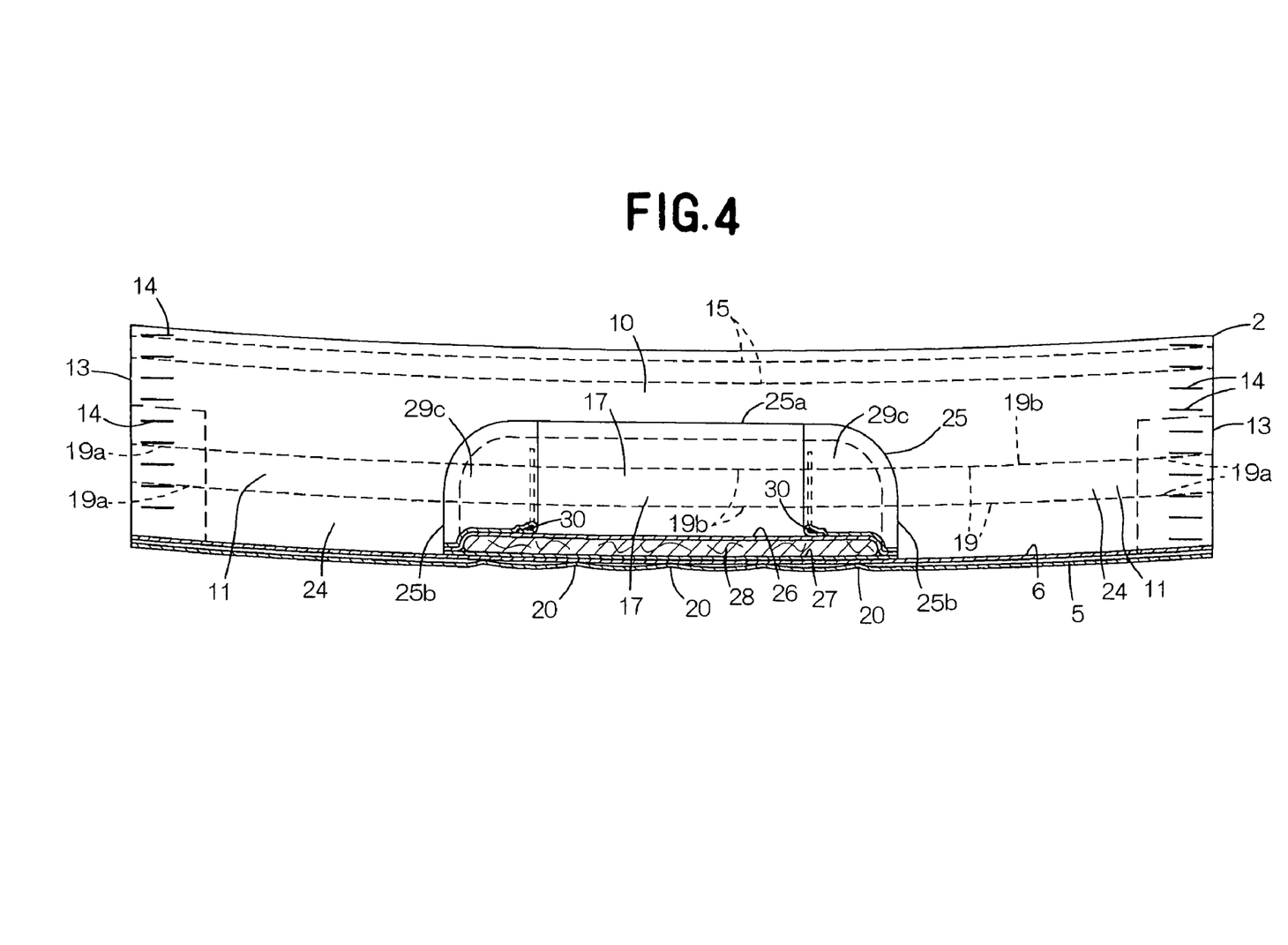
FIG. 4 is a cross-sectional view taken along a line IV-IV in FIG. 2.

FIG. 1 is a partially cutaway perspective view of a disposable wearing article, FIG. 2 is a plan view showing the article of FIG. 1 as disconnected in front and rear waist regions, FIG. 3 is a cross-sectional view showing the article as slightly curved, along a line III-III in FIG. 2 and FIG. 4 is a cross-sectional view showing the article along a line IV-IV in FIG. 2. In FIG. 1, a waist-surrounding direction is indicated by an arrow X, a longitudinal direction is indicated by an arrow Y and a thigh-surrounding direction is indicated by an arrow Z. In FIG. 2, chain double-dashed lines indicate auxiliary elastic members in an unstretched state.

The article 1 comprises front and rear waist regions 7, 9 opposed to each other and a crotch region 8 lying between these waist region 7, 9 wherein a waist-hole 3 and a pair of leg-holes 4 below the waist-hole 3 are defined. The article 1 is basically composed of a chassis 2 and an absorbent structure 25 disposed to an inner side of the chassis 2.

The chassis 2 comprises a breathable outer sheet 5 facing a garment and a breathable inner sheet 6 facing a wearer's body.

The outer and inner sheets 5, 6 may be liquid-impervious so far as one of these sheets is breathable at least. The chassis 2 has waist-hole's peripheral portions 10 lying outside longitudinally opposite ends 25a of the absorbent structure 25 in the front and rear waist regions 7, 9, waist's opposite side portions 11 lying outside transversely opposite side edges 25b of the absorbent structure 25 in the front and rear waist regions 7, 9 and leg-holes' peripheral portions 12 lying outside the side edges 25b of the absorbent structure 25 in the crotch region 8. The outer sheet 5 and the inner sheet 6 of the chassis 2 have respective inner surfaces joined together along those edges. Furthermore, side edges 13 contiguous to the waist's opposite side portions 11 of the outer and inner sheets 5, 6 are overlaid and joined together by means of a plurality of heat-sealing means 14 arranged intermittently in the longitudinal direction so as to define a waist-hole and a pair of leg-holes.

The waist-hole's peripheral portions 10 are provided with a plurality of waist-surrounding elastic members 15 which are secured thereto in a stretched state in the waist-surrounding direction so that a plurality of gathers are formed there as the elastic members contract. Similarly, the leg-holes' peripheral portions 12 are respectively provided with a plurality of thigh-surrounding elastic members 16 which are secured thereto in a stretched state in the thigh-surrounding direction so that a plurality of gathers are formed there as the elastic members contract. In this way, both the waist-surrounding elastic members 15 and the thigh-surrounding elastic members 16 to form gathers are interposed between the outer sheet 5 and the inner sheet 6 of the chassis 2 and secured thereto.

In the front waist region 7, the outer sheet 5 has a picture 18 (figure) of bear cub as a fancy element depicted on its outer surface in an area 17 occupied with the absorbent structure 25. The picture 18 may be depicted on which of the inner surface of the outer sheet 5 and the inner or outer surface of the inner sheet 6 so far as the picture 18 can be seen from the outside of the outer sheet 5.

The front and rear waist regions 7, 9 are provided with a plurality of auxiliary elastic members 19 which are extending across the absorbent structure 25 in the waist-surrounding direction and secured thereto in a stretched state. The auxiliary elastic members 19 are interposed between the outer sheet 5 and the inner sheet 6 of the chassis 2 and sideways arranged between the waist-hole's peripheral portions 10 and the leg-holes 4, being spaced one from another by a dimension given in the longitudinal direction. Each of the auxiliary elastic members 19 has longitudinally opposite end portions 19a which are secured to the chassis 2 in the vicinity of the side edges 13 thereof contiguous to the waist's opposite side portions 11 and an intermediate portion 19b which is lying between the opposite end portions 19a and not secured, that is, free to the chassis 2. As best seen in FIG. 2, a length L1 of the auxiliary elastic members 19 as measured in the waist-surrounding direction in a contracting or unstretched state is slightly larger than a length L2 of the absorbent structure 25 lying in the front and rear waist regions 7, 9 as measured in the waist-surrounding direction. The length L1 is larger than the length L2 preferably by 1-5 mm. It is also possible without departing from the scope of this invention that the length L1 of the auxiliary elastic members 19 as measured in the waist-surrounding direction in an unstretched state is substantially equal to the length L2 of the absorbent structure 25 as measured in the waist-surrounding direction.

In the front and rear waist regions 7, 9, the outer sheet 5 and the inner sheet 6 of the chassis 2 have respective inner surfaces joined together at a plurality of joining sites 20. Taking a broad view, these joining sites 20 are in the form of a dot and provided in the area 17 which is occupied with the absorbent structure 25 in the front and rear waist regions 7, 9. These joining sites 20 are arranged between the auxiliary elastic members 19, being spaced one from another in the longitudinal direction as well as in the waist-surrounding direction. The joining sites 20 consist of first joining sites 21 arranged in the longitudinal direction in a middle zone of the absorbent structure 25, second joining sites 22 arranged in the longitudinal direction on both sides of the first joining sites 21 and third joining sites 23 arranged in the longitudinal direction in the vicinity of the transversely opposite side edges 25b of the absorbent structure 25. Of the first and second joining sites 21, 22, the uppermost joining sites 21a, 22a in the front and rear waist regions 7, 9, respectively, are distributed between the respective auxiliary elastic members 19c which are extending across the absorbent structure 25 in the vicinity of the longitudinally opposite ends 25a of the absorbent structure 25 and the respective opposite ends 25a of the absorbent structures 25. Of the third joining sites 23, the uppermost joining sites 23a in the front and rear waist regions 7, 9 are distributed at cross-points of the longitudinally opposite ends 25a of the absorbent structure 25 and the transversely opposite side edges 25b of the absorbent structure 25. The number of the joining sites 20 arranged in the longitudinal direction is not limited to the number shown in figures. The joining sites 20 may be in the form of line sections or band sections both extending in the waist-surrounding direction. The first and second joining sites 21, 22 are not essential so far as the outer sheet 5 and the inner sheet 6 have respective inner surfaces joined together at the third joining sites 23. Also in an area 24 which is not occupied with the absorbent structure 25 in the front and rear waist regions 7, 9, the outer sheet 5 and the inner sheet 6 may have respective inner surfaces joined together at the joining sites 20 arranged thereon, being spaced from one from another by a dimension given in the longitudinal direction. In this case, the joining sites 20 are similarly provided between the auxiliary elastic members 19.

The absorbent structure 25 comprises a liquid-pervious inner sheet 26 facing a wearer's body, a substantially liquid-impervious outer sheet 27 disposed to the back side thereof and a liquid-absorbent core 28 interposed between these sheets 26, 27 which are formed in the form of a pad. In the case that the absorbent structure 25 is formed in the form of a pad, the chassis 2 may not have the crotch region 8 so that the front and rear waist regions 7, 9 are separated, although not shown in figures. It is because that the absorbent structure 25 including the liquid-impervious outer sheet 27 connects the front and rear waist regions 7, 9 of the chassis 2. The absorbent structure 25 has a substantially rectangular planar shape and extends across the crotch region 8 into the front and rear waist regions 7, 9 and the core 28 is joined to at least one of the inner and outer sheets 26, 27. The core 28 comprises a mixture of fluff pulp and super-absorbent polymer particles or a mixture of fluff pulp, super-absorbent polymer particles and thermoplastic synthetic resin fiber, in both cases, compressed to a desired thickness. Consequently, the core 28 presents its stiffness higher than those of the chassis 2, the inner and outer sheets 26, 27. Preferably, the liquid-absorbent core 28 is entirely covered with a liquid-absorbent sheet such as a tissue paper in order to prevent the core 28 from getting out of shape and to prevent the polymer particles from falling off. The polymer particles may be selected from a group of publicly-known materials consisting of starch-based polymer, cellulose-based polymer and synthetic polymer. Peripheral edge portions of the inner and outer sheets 26, 27 extending outward beyond a peripheral edge of the core 28 are overlaid and joined together. Substantially entire area of the absorbent structure 25 lying in the front and rear waist regions 7, 9 is bonded to the inner sheet 6 of the chassis 2 by means of the outer sheet 27. The absorbent structure 25 is provided in the vicinity of its transversely opposite side edges 25b with substantially liquid-impervious barrier flaps 29. The barrier flaps 29 respectively have fixed side edge portions 29a which are extending along the transversely opposite side edges 25b of the absorbent structure 25 and fixed thereto, free side edge portions 29b which are extending in parallel to the fixed side edge portions 29a and fixed longitudinally opposite end portions 29c which are collapsed toward the transversely middle area of the absorbent structure 25 and fixed to the absorbent structure 25 in the vicinity of its longitudinally opposite ends 25a. The free side edge portions 29b are respectively provided with stretchable elastic members 30 which are extending along the free side edge portions 29b and attached thereto in a stretched state.

As the article 1 is longitudinally curved with the inner sheet 26 inside, the stretchable elastic members 30 contract and the free side edge portions 29b of the respective barrier flaps 29 rise on the inner sheet 26. consequently, these free side edge portions 29b form barriers against bodily discharges and prevent bodily discharges from leaking beyond the transversely opposite side edges 25b of the absorbent structure 25.

Joining of the outer and inner sheets 5, 6 of the chassis 2, bonding of the elastic members 15, 16, 19 to the outer and inner sheets 5, 6, joining of the inner and outer sheets 26, 27, and bonding of the core 28 to the inner and outer sheets 26, 27 are carried out using a publicly-known hot melt adhesive (not shown).

As for the first embodiment mentioned above, the intermediate portions 19b of the respective auxiliary elastic members 19 are secured neither to the outer sheet 5 nor to the inner sheet 6 and therefore a plurality of gathers are not formed on the outer sheet 5 and the inner sheet 6 except for the waist-hole's peripheral portions 10, the vicinity of the side edges 13 contiguous to the waist's opposite side portions 11 and the leg-holes' peripheral portions 12 where a contractile force of the waist- and thigh-surrounding members 15, 16 acts on. Touch as well as appearance of the chassis 2 can be improved thereby. In the area 17 which is occupied with the absorbent structure 25, the absorbent structure 25 is joined to the inner sheet 6 extending in the front and rear waist regions 7, 9 and the outer sheet 5 and the inner sheet 6 have respective inner surfaces joined together at a plurality of joining sites 20. Consequently the stiffness of the absorbent structure 25 prevents a contractile force of the auxiliary elastic members 19 in the waist-surrounding direction from acting on the outer sheet 5 and the inner sheet 6. In the area 17 which is occupied with the absorbent structure 25, the outer sheet 5 is kept substantially flat and therefore the picture 18 of bear cub depicted on the outer sheet 5 as an example is not distorted and distinctly recognized.

If the length L1 of the auxiliary elastic members 19 as measured in the waist-surrounding direction in a contracting or unstretched state is larger than that of the absorbent structure 25 as measured between its opposite side edges 25b in the waist-surrounding direction by 1-5 mm, the auxiliary elastic members 19 can not contract to a length shorter than the length L2 of the absorbent structure 25 as measured in the waist-surrounding direction, and no wrinkle can be formed in the absorbent structures 25 by the contractile force of the auxiliary elastic members 19 even when these auxiliary elastic members 19 contract in the waist-surrounding direction.

A plurality of the joining sites 20 which are arranged between the auxiliary elastic members 19 prevent these auxiliary elastic members 19 from moving in the longitudinal direction. Since the joining sites 21a, 22a, 23a are distributed between the auxiliary elastic members 19c which are extending across the absorbent structure 25 in the vicinity of its longitudinally opposite ends 25a and these ends 25a of the absorbent structure 25, these auxiliary elastic members 19c can not move outward beyond the longitudinally opposite ends 25a of the absorbent structure 25. These auxiliary elastic members 19c support the absorbent structure 25 in the vicinity of its longitudinally opposite ends 25a and therefore there is no possibility that the absorbent structure 25 might protrude in its longitudinally opposite ends 25a outward from the chassis 2.

The article 1 has, in addition to the waist-surrounding elastic members 15, a plurality of the auxiliary elastic members 19 in the front and rear waist regions 7, 9 so that these elastic members 15, 19 may tighten the wearer's torso. Consequently the front and rear waist regions 7, 9 of the article 1 can be put in close contact with the wearer's body so as to prevent the article 1 from slipping down and to prevent bodily discharges from leaking out.

Figure 5:
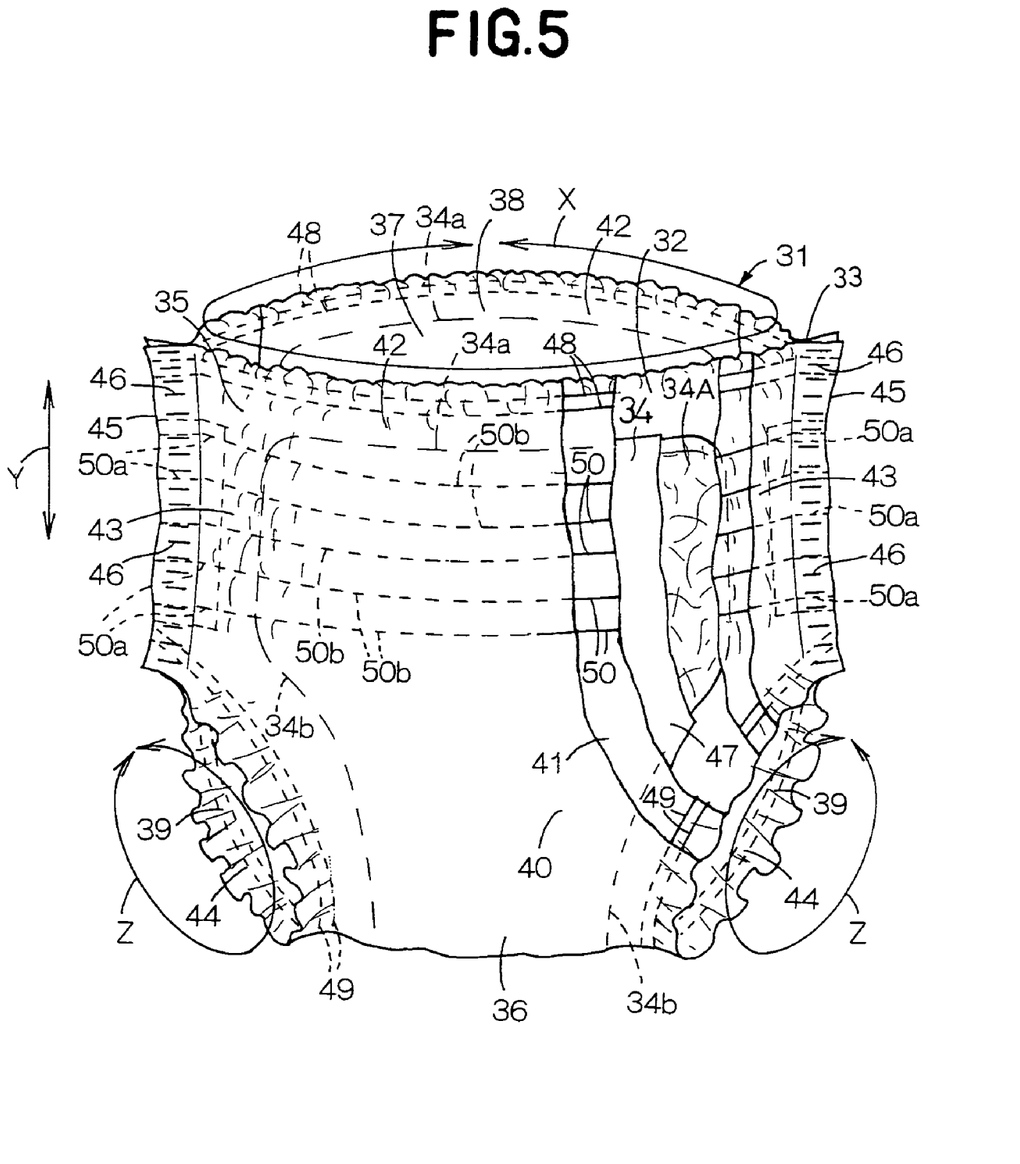
FIG. 5 is a partially cutaway perspective view showing another embodiment of the disposable wearing article according to this invention.
Figure 6:
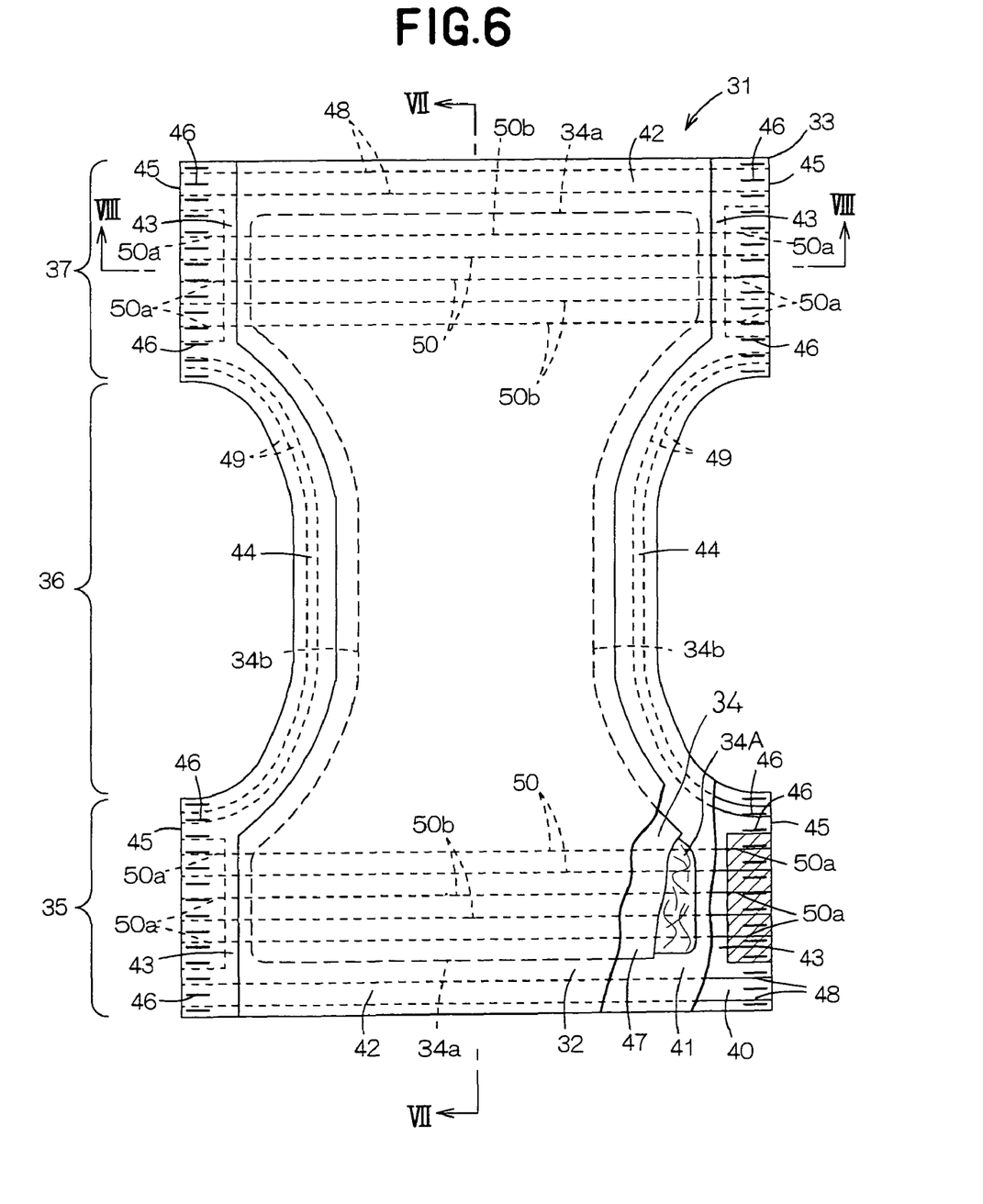
FIG. 6 is a plan view showing the article of FIG. 5 as developed in the longitudinal direction.
Figure 7:
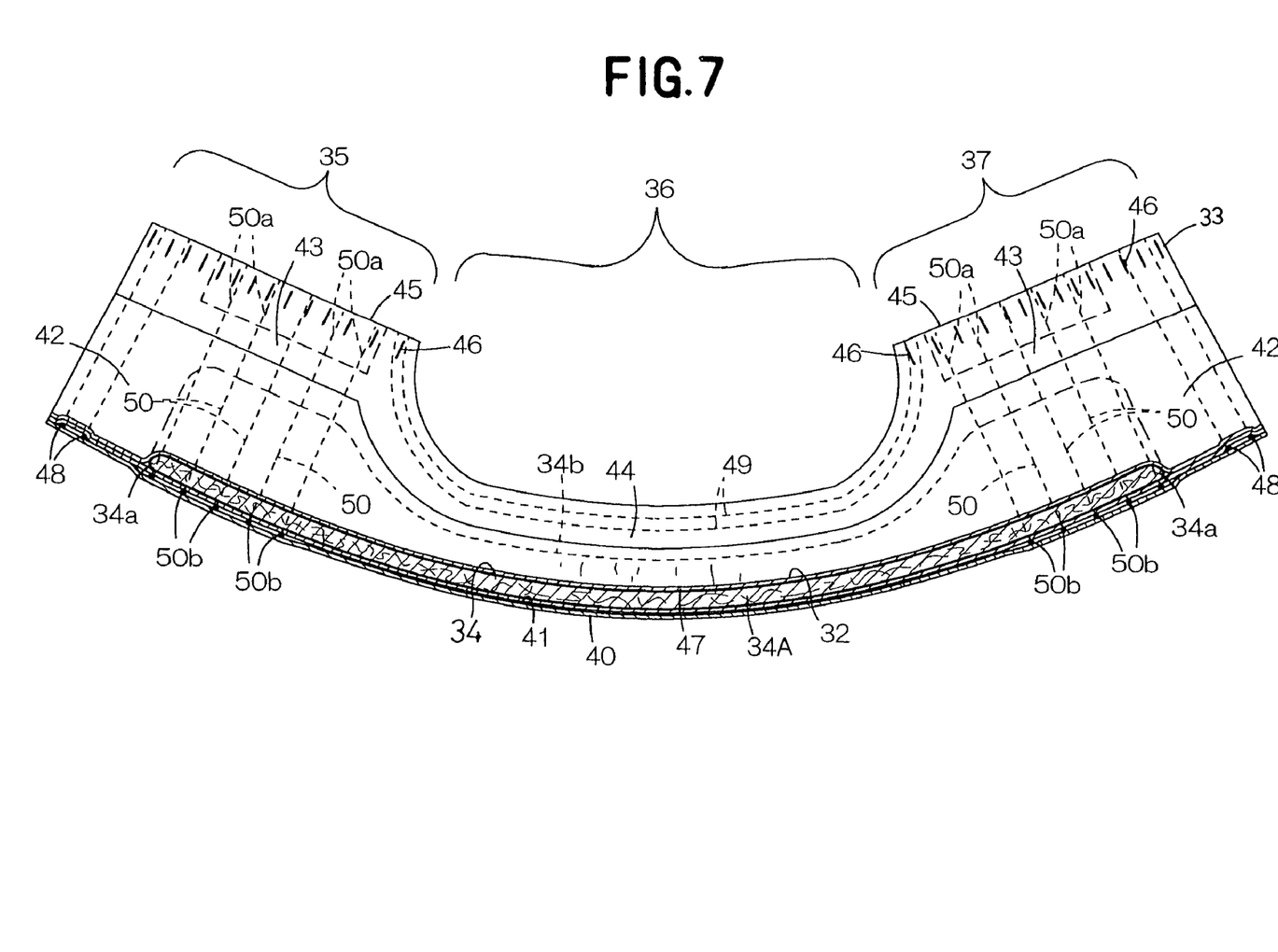
FIG. 7 is a cross-sectional view taken along a line VII-VII in FIG. 6.
Figure 8:
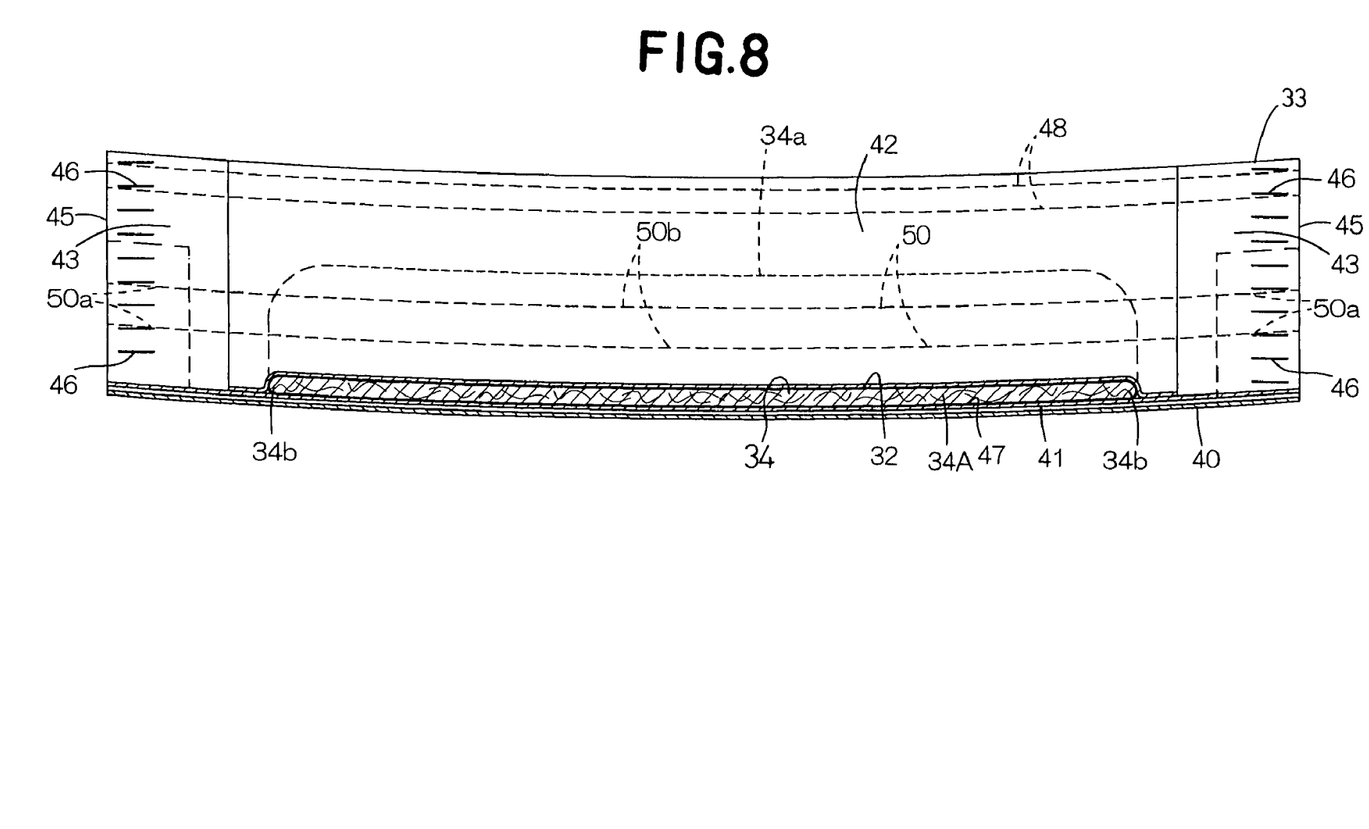
FIG. 8 is a cross-sectional view taken along a line VIII-VIII in FIG. 6.

The second embodiment according to this invention is illustrated in FIGS. 5-8. FIG. 5 is a partially cutaway perspective view of the disposable wearing article according to this invention, FIG. 6 is a plan view showing the article of FIG. 5 as disconnected in the front and rear waist region, FIG. 7 is a cross-sectional view showing the article as slightly curved along a line VII-VII in FIG. 6 and FIG. 8 is a cross-sectional view showing the article along the line VIII-VIII in FIG. 6. In FIG. 5, the waist-surrounding direction is indicated by an arrow X, the longitudinal direction is indicated by an arrow Y and the thigh-surrounding direction is indicated by an arrow Z.

The article 31 comprises front and rear waist regions 35, 37 opposed to each other and a crotch region 36 lying between these front and rear waist regions 35, 37 wherein a waist-hole 38 and a pair of leg-holes 39 are defined.

The article 31 is basically composed of a chassis 33 and an absorbent structure 34. The chassis 33 comprises a breathable outer sheet 40 facing a garment and a substantially liquid-impervious inner sheet 41. The chassis 33 have waist-hole's peripheral end portions 42 lying outside longitudinally opposite ends 34a of the absorbent structure 34 in the front and rear waist regions 35, 37, waist's side portions 43 lying outside transversely opposite side edges 34b of the absorbent structure 34 in the front and rear waist regions 35, 37 and leg-holes' peripheral edge portions 44 lying outside the side edges 34b of the absorbent structure 34 in the crotch region 36.

The outer sheet 40 and the inner sheet 41 of the chassis 33 have respective inner surfaces joined together along those edges. Furthermore, the side edges 45 contiguous to the waist's opposite side portions 43 of the outer and inner sheets 40, 41 are overlaid and joined together by means of a plurality of heat-sealing means 46 arranged intermittently in the longitudinal direction so as to define a waist-hole 38 and a pair of leg-holes 39.

The absorbent structure 34 extends across the crotch region 36 into the front and rear waist regions 35, 37 and is composed of a liquid-pervious inner sheet 32 facing a wearer's body and a liquid-absorbent core 34A covered with the inner sheet 32. The absorbent structure 34 is the same as the core 28 of the absorbent structure 25 in the first embodiment and presents its stiffness higher than those of the inner sheet 32 and the chassis 33. The liquid-absorbent core 34A is entirely covered with a liquid-pervious sheet 47 such as a tissue paper and is bonded in a substantially entire area of its lower portion to the inner sheet 41 of the chassis 33 extending in the front and rear waist regions 35, 37 and the crotch region 36 by means of the sheet 47. The inner sheet 32 has its dimension in the waist-surrounding direction smaller than that of the chassis 33 and its peripheral portion extending outward from the peripheral edge of the liquid-absorbent core 34A is bonded to the outer surface of the inner sheet 41.

The waist-hole's peripheral portions 42 are provided with a plurality of waist-surrounding elastic members 48 which is extending in the waist-surrounding direction and attached thereto in a stretched state. The leg-holes' peripheral portions 44 are respectively provided with a plurality of thigh-surrounding elastic members 49 which is extending in the thigh-surrounding direction and attached thereto in a stretched state. Both the waist-surrounding elastic members 48 and the thigh-surrounding elastic members 49 are interposed between the outer sheet 40 and the inner sheet 41 of the chassis 33 and secured to respective inner surfaces of these sheets 40, 41.

The front and rear waist regions 35, 37 are provided with a plurality of auxiliary elastic members 50 which is extending across the absorbent structure 34 in the waist-surrounding direction and attached thereto in a stretched state. The auxiliary elastic members 50 are interposed between the outer sheet 40 and the inner sheet 41 and arranged between the waist-hole's peripheral portions 42 and the leg-holes 39, being spaced one from another by a dimension given in the longitudinal direction. Each of the auxiliary elastic members 50 has longitudinally opposite end portions 50a which are secured to the chassis 33 in the vicinity of the side edges 45 contiguous to the respective waist's opposite side portions 43 and an intermediate portion 50b which is lying between the longitudinally opposite end portions 50a and not secured, that is, free to the chassis 33. Preferably, a length of the auxiliary elastic members 50 as measured in the waist-surrounding direction in a contracting or unstretched state is equal to or larger than that of the absorbent structure 34 by 1-5 mm.

Joining of the outer sheet 40 and the inner sheet 41 of the chassis 33, securing the elastic members 48, 49, 50 to the outer and inner sheets 40, 41, and joining of the inner sheet 32 and the absorbent structure 34 to the inner sheet 41 are carried out using a publicly-known hot melt adhesive (not shown).

In the article 31, when the auxiliary elastic members 50 contract in the waist-surrounding direction, the chassis 33 extending in the front and rear waist regions 35, 37 rises gently, but a plurality of fine gathers are not formed in the chassis 33 except for the waist-hole's peripheral portions 42, the vicinity of the side edges 45 contiguous to the waist's opposite side portions 43 and the leg-holes' peripheral portions 44 where a contractile force of the waist- and thigh-surrounding elastic members 48, 49 acts on because the intermediate portions 50b of the auxiliary elastic members 50 are secured to the chassis 33. When these auxiliary elastic members 50 contract in the waist-surrounding direction, the auxiliary elastic members 50 can not contract to a length shorter than the length of the absorbent structure 34 as measured in the waist-surrounding direction and therefore no wrinkle is formed in the absorbent structure 34 by the stretch stress of the auxiliary elastic members 50.

A stock material for the inner sheets 26, 32 may be selected from a group including a fibrous nonwoven fabric treated to become hydrophilic, a thermoplastic film having a plurality of fine pores and hydrophobic fibrous nonwoven fabric. The outer sheet 5, 40 and the inner sheets 6, 41 and the outer sheet 27 may be formed using a material selected from a group of materials including a substantially liquid-impervious hydrophobic fibrous nonwoven fabric, a breathable but liquid-impervious thermoplastic film, a composite nonwoven fabric consisting of two or more layers of a hydrophobic fibrous nonwoven fabric laminated one with another and a composite sheet consisting of a hydrophobic nonwoven fabric and a breathable but liquid-impervious thermoplastic film.

Nonwoven fabric may be selected from a group of materials including products obtained by spun lacing, needle punching, melt blowing, thermal bonding, spun bonding, chemical bonding and air-through processes. Component fibers of the nonwoven fabric may be selected from a group of materials including polyolefine-, polyester- and polyamide-based fibers and core-sheath-type and side-by-side-type conjugated fibers of polyethylene/polypropylene and polyethylene/polyester.

In the disposable wearing article according to this invention, the intermediate portions of the auxiliary elastic members are secured to the chassis and therefore a plurality of fine gathers are not formed in the chassis except for the waist-hole's peripheral end portions, the vicinity of the side edges contiguous to the waist's side portions and the leg-holes' peripheral portions where a contractile force of the waist- and thigh-surrounding elastic members acts on. Touch as well as appearance of the chassis can be improved thereby.

In the embodiment of this invention arranged so that the outer sheet and the inner sheet which are defining the chassis have respective opposed surfaces joined together at a plurality of the joining sites arranged between the auxiliary elastic members in the longitudinal direction, when the auxiliary elastic members contract in the waist-surrounding direction, the stiffness of the absorbent structure prevents the contractile force of the auxiliary elastic members from acting on the chassis in the area occupied by the absorbent structure, and the outer sheet of the chassis is kept substantially flat in the area occupied by the absorbent structure.

In the embodiment of this invention arranged so that the length of the auxiliary elastic members as measured in the waist-surrounding direction in an unstretched state is substantially equal to or slightly larger than the length of the absorbent structure as measured between its opposite side edges in the waist-surrounding direction, when the auxiliary elastic members contract in the waist-surrounding direction, the auxiliary elastic members can not contract to a length shorter than the length of the absorbent structure as measured in the waist-surrounding direction and no wrinkle is formed in the structure by the contractile force of the auxiliary elastic members.

In the embodiment of this invention arranged so that a fancy element is depicted on the chassis in the area occupied with the structure, a plurality of fine gathers are not formed on the outer sheet of the chassis in the area occupied with the structure and therefore the fancy element is not distorted and can be distinctly recognized.

What is claimed is:

1. A pants-type disposable wearing article, comprising:
    a longitudinal direction,
    a waist-surrounding direction orthogonal to said longitudinal direction,
    a chassis defining a front waist region, a rear waist region, a crotch region extending in said longitudinal direction between said front and rear waist regions, an elasticized waist-hole, and a pair of elasticized leg-holes,
    an absorbent structure extending on an inner surface of said chassis between said front and rear waist regions, and
    a plurality of auxiliary elastic members secured to said chassis in a stretched state and extending in said waist surrounding direction so as to cross said absorbent structure in at least one of said front and rear waist regions, each of said auxiliary elastic members having, in said waist surrounding direction, opposite end portions and a middle portion located between said opposite end portions,
    said opposite end portions being secured to said chassis in vicinities of transversely opposite side edges of the one of said front and rear waist regions while said middle portion being free of direct securement to said chassis in the one of said front and rear waist regions,
    wherein
    said chassis comprises an outer sheet and an inner sheet directly joined together at a plurality of joining sites;
    said plurality of auxiliary elastic members are interposed between said outer and inner sheets;
    said plurality of joining sites are distributed at least in an area of said absorbent structure in the one of front and rear waist regions, are spaced one from another by given space in said longitudinal direction and are located between the middle portions of said auxiliary elastic members;
    each of said auxiliary elastic members is entirely free of direct attachment to said chassis except at the opposite end portions of said auxiliary elastic member; and
    the joining sites are each in the form of a dot and comprise
        first joining sites arranged in the longitudinal direction in a middle zone of the absorbent structure,
        second joining sites arranged in the longitudinal direction on both sides of the first joining sites, and
        third joining sites arranged in the longitudinal direction on both sides of the second joining sites and in the vicinity of the transversely opposite side edges of the absorbent structure.

2. The article according to claim 1, wherein said absorbent structure comprises
    a liquid-pervious inner sheet adapted to face a wearer's body,
    a substantially liquid-impervious outer sheet bonded to the inner sheet of said chassis, and
    a liquid-absorbent core disposed between said liquid-pervious inner sheet and said substantially liquid-impervious outer sheet, wherein said substantially liquid-impervious outer sheet is disposed between the liquid-absorbent core and the inner sheet of said chassis.

3. The article according to claim 1, wherein said absorbent structure comprises
    a liquid-pervious inner sheet, and
    a liquid-absorbent core having a top surface thereof covered with said liquid-pervious inner sheet and a back surface thereof covered with said chassis.

4. The article according to claim 1, wherein said front and rear waist regions of said chassis are permanently joined to each other at the transversely opposite side edges thereof to define said elasticized waist-hole and elasticized leg-holes.

5. The article according to claim 1, further comprising a pair of leakage-barrier flaps that extend along transversely opposite side edges of said absorbent structure.

6. The article according to claim 1, wherein a length of said auxiliary elastic members in the waist-surrounding direction as measured in a contracted, unstretched state thereof is equal to a width of the absorbent structure in the one of said front and rear waist regions.

7. The article according to claim 1, wherein a length of said auxiliary elastic members in the waist-surrounding direction as measured in a contracted, unstretched state thereof is greater than a width of the absorbent structure in the waist-surrounding direction in the one of said front and rear waist regions by 1-5 mm.

8. The article according to claim 1, wherein
    the middle portion of each of said auxiliary elastic members connects the opposite end portions of said auxiliary elastic member, and extends across an entire width of said absorbent structure in the waist-surrounding direction from one of transversely opposite side edges of said absorbent structure to the other; and
    an entire section of said middle portion which is located between the transversely opposite side edges of said absorbent structure is directly bonded neither to the inner sheet nor to the outer sheet.

9. The article according to claim 8, wherein said joining sites are distributed between every pair of adjacent said auxiliary elastic members and all said joining sites are distributed between the transversely opposite side edges of said absorbent structure.

10. The article of claim 9, wherein said joining sites define limits of displacement of the middle portions of said auxiliary elastic members in the longitudinal direction, without affecting contractibility of said middle portions in the waist-surrounding direction.

11. The article according to claim 10, further comprising, in the one of said front and rear waist regions, a picture on said chassis in an area underlying said absorbent structure.

12. The article of claim 11, wherein the middle portions of some of said auxiliary elastic members underlie and extend across said picture without causing gathers to be formed in the area of said chassis, thereby preventing the picture in said area from being distorted.

13. The article of claim 12, wherein all said auxiliary elastic members are disposed between and spaced in the longitudinal direction from said elasticized waist hole and said elasticized leg holes.

14. The article of claim 10, wherein an entire area of said chassis, which underlies said absorbent structure and across which said auxiliary elastic members extend, are substantially free of gathers.

15. The article of claim 10, wherein some of the joining sites are disposed, in the longitudinal direction, between the middle portion of a topmost one of the auxiliary elastic members and a longitudinal end of the absorbent structure in said at least one of said front and rear waist regions so as to prevent the middle portions of the topmost auxiliary elastic member from moving in the longitudinal direction beyond said longitudinal end of the absorbent structure;

the topmost auxiliary elastic member being closest, in the longitudinal direction, to the waist-hole among all said auxiliary elastic members; and said longitudinal end of the absorbent structure being located, in the longitudinal direction, between the topmost auxiliary elastic member and the waist-hole.

16. The article of claim 2, wherein said inner and outer sheets of said chassis are both liquid-impervious.

17. The article of claim 16, wherein said inner and outer sheets of said chassis are coextensive throughout their entireties.

18. A pants-type disposable wearing article, comprising:
a longitudinal direction,
a waist-surrounding direction orthogonal to said longitudinal direction,
a chassis defining a front waist region, a rear waist region, a crotch region extending in said longitudinal direction between said front and rear waist regions, an elasticized waist-hole, and a pair of elasticized leg-holes,
an absorbent structure extending on an inner surface of said chassis between said front and rear waist regions, and
a plurality of auxiliary elastic members secured to said chassis in a stretched state and extending in said waist surrounding direction so as to cross said absorbent structure in at least one of said front and rear waist regions, each of said auxiliary elastic members having, in said waist surrounding direction, opposite end portions and a middle portion located between said opposite end portions,
said opposite end portions being secured to said chassis in vicinities of transversely opposite side edges of the one of said front and rear waist regions while said middle portion being free of direct securement to said chassis in the one of said front and rear waist regions,
wherein
said chassis comprises an outer sheet and an inner sheet directly joined together at a plurality of joining sites;
said plurality of auxiliary elastic members are interposed between said outer and inner sheets;
said plurality of joining sites are distributed at least in an area of said absorbent structure in the one of front and rear waist regions, are spaced one from another by given space in said longitudinal direction and are located between the middle portions of said auxiliary elastic members;

each of said auxiliary elastic members is entirely free of direct attachment to said chassis except at the opposite end portions of said auxiliary elastic member;
the joining sites are each in the form of a dot and are all arranged only along and in vicinities of the transversely opposite side edges of said absorbent structure in the one of the front and rear waist regions; and
a number of said joining sites are located between the middle portions of adjacent said auxiliary elastic members.

19. The article according to claim 18, wherein a length of each of said auxiliary elastic members in the waist-surrounding direction as measured in an unstretched state thereof is substantially equal to a width of the absorbent structure in the waist-surrounding direction in the one of said front and rear waist regions.

20. The article according to claim 18, wherein
the middle portion of each of said auxiliary elastic members connects the opposite end portions of said auxiliary elastic member, and extends across an entire width of said absorbent structure in the waist-surrounding direction from one of transversely opposite side edges of said absorbent structure to the other; and
an entire section of said middle portion which is located between the transversely opposite side edges of said absorbent structure is directly bonded neither to the inner sheet nor to the outer sheet.

21. The article according to claim 20, wherein said joining sites are distributed between every pair of adjacent said auxiliary elastic members and all said joining sites are distributed between the transversely opposite side edges of said absorbent structure.

22. The article of claim 21, wherein said joining sites define limits of displacement of the middle portions of said auxiliary elastic members in the longitudinal direction, without affecting contractibility of said middle portions in the waist-surrounding direction.

23. The article of claim 22, wherein some of the joining sites are disposed, in the longitudinal direction, between the middle portion of a topmost one of the auxiliary elastic members and a longitudinal end of the absorbent structure in said at least one of said front and rear waist regions so as to prevent the middle portions of the topmost auxiliary elastic member from moving in the longitudinal direction beyond said longitudinal end of the absorbent structure;

the topmost auxiliary elastic member being closest, in the longitudinal direction, to the waist-hole among all said auxiliary elastic members; and said longitudinal end of the absorbent structure being located, in the longitudinal direction, between the topmost auxiliary elastic member and the waist-hole.

24. The article of claim 23, wherein said length of said auxiliary elastic members in the waist-surrounding direction as measured in the unstretched state thereof is less than a half of a circumference of the waist hole.

* * * * *